US011550014B2

(12) United States Patent
Ennis et al.

(10) Patent No.: US 11,550,014 B2
(45) Date of Patent: Jan. 10, 2023

(54) ARTIFICIAL INTELLIGENCE BASED RECONSTRUCTION FOR PHASE CONTRAST MAGNETIC RESONANCE IMAGING

(71) Applicants: The Board of Trustees of the Leland Stanford Junior University, Stanford, CA (US); The United States of America as represented by The Department Of Veterans Affairs, Washington, DC (US)

(72) Inventors: Daniel B. Ennis, Palo Alto, CA (US); Matthew J. Middione, St. George, UT (US); Julio A. Oscanoa Aida, Stanford, CA (US); Shreyas S. Vasanawala, Stanford, CA (US)

(73) Assignees: The Board of Trustees of the Leland Stanford Junior University, Stanford, CA (US); The United States of America as represented by The Department Of Veterans Affairs, Washington, DC (US)

( * ) Notice: Subject to any disclaimer, the term of this patent is extended or adjusted under 35 U.S.C. 154(b) by 0 days.

(21) Appl. No.: 17/673,003

(22) Filed: Feb. 16, 2022

(65) Prior Publication Data
US 2022/0260660 A1 Aug. 18, 2022

Related U.S. Application Data

(60) Provisional application No. 63/149,670, filed on Feb. 16, 2021.

(51) Int. Cl.
*G01R 33/563* (2006.01)
*G01R 33/56* (2006.01)
(Continued)

(52) U.S. Cl.
CPC ........ *G01R 33/5635* (2013.01); *A61B 5/0263* (2013.01); *A61B 5/7267* (2013.01); *G01R 33/5608* (2013.01); *G06N 3/0454* (2013.01)

(58) Field of Classification Search
CPC A61B 5/0263; A61B 5/7267; G01R 33/5608; G01R 33/5635; G06N 3/0454
See application file for complete search history.

(56) References Cited

U.S. PATENT DOCUMENTS 10,534,059 B2 * 1/2020 Rich .................. G01R 33/5608
10,712,416 B1 7/2020 Sandino
(Continued)

OTHER PUBLICATIONS

Haji-Valizadeh et al. Highly accelerated free-breathing real-time phase contrast cardiovascular MRI via complex-difference deep learning. Magn Reson Med 2021;86(2):804-819.
(Continued)

*Primary Examiner* — Gregory H Curran
(74) *Attorney, Agent, or Firm* — Lumen Patent Firm

(57) ABSTRACT

A method for phase-contrast magnetic resonance imaging (PC-MRI) acquires undersampled PC-MRI data using a magnetic resonance imaging scanner and reconstructs MRI images from the undersampled PC-MRI data by reconstructing a first flow-encoded image using a first convolutional neural network, reconstructing a complex difference image using a second convolutional neural network, combining the complex difference image and the first flow-encoded image to obtain a second flow-encoded image, and generating a velocity encoded image from the first flow-encoded image and second flow-encoded image using phase difference processing.

7 Claims, 16 Drawing Sheets

(51) Int. Cl.
*G06N 3/04* (2006.01)
*A61B 5/00* (2006.01)
*A61B 5/026* (2006.01)

(56) References Cited

U.S. PATENT DOCUMENTS

2019/0053735 A1* 2/2019 Hu .................... A61B 5/055
2020/0035290 A1* 1/2020 Ho .................... G11C 11/4093

OTHER PUBLICATIONS

Sandino et al., Accelerating cardiac cine MRI using a deep learning-based ESPIRiT reconstruction. May 18, 2020. arXiv:1911.05845 [eess.SP] as submitted to Magnetic resonance in medicine 2021;85(1):152-167.

* cited by examiner

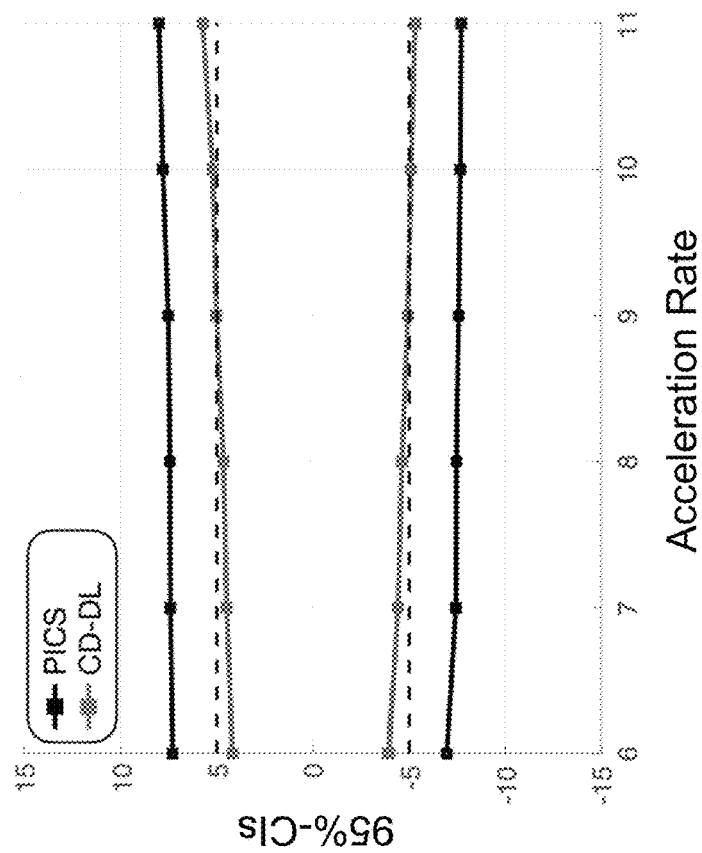
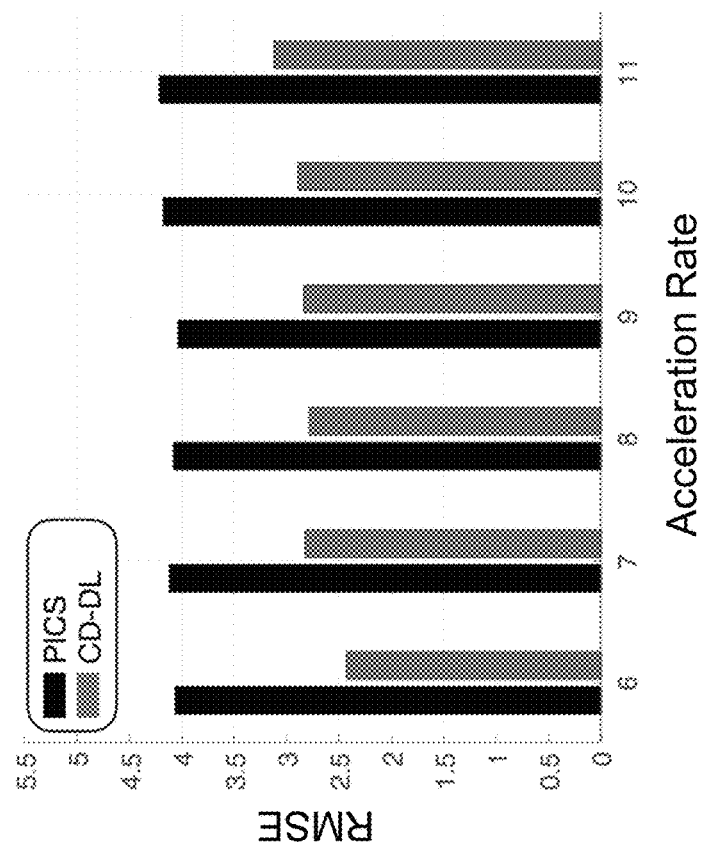

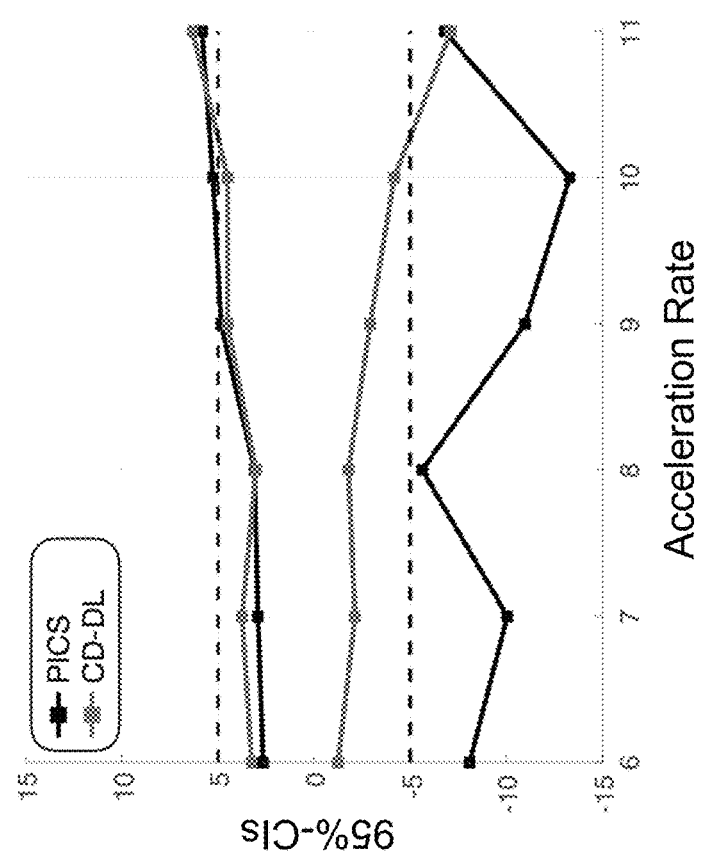
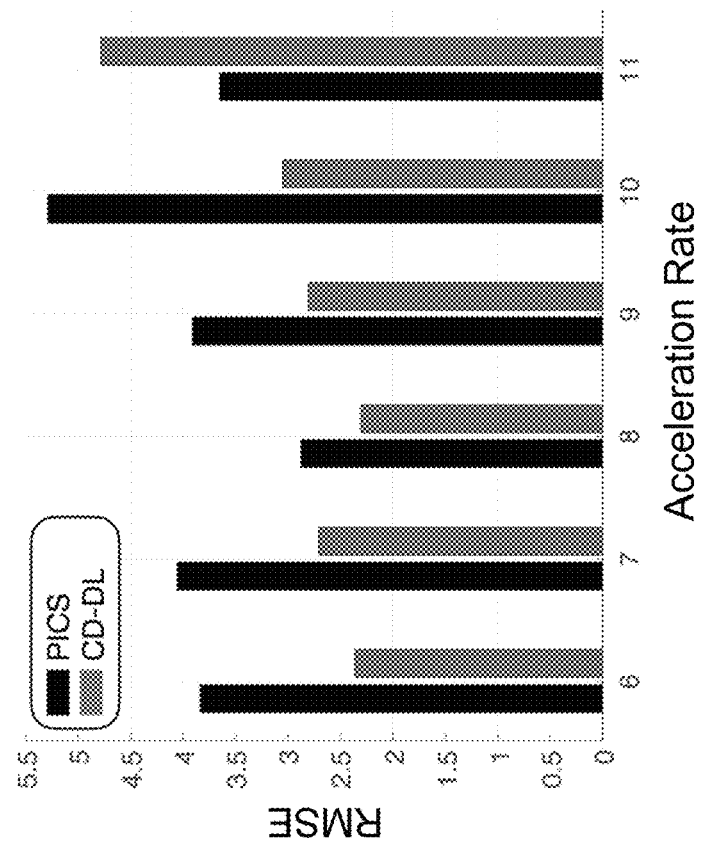
Fig. 3D
Fig. 3C

ARTIFICIAL INTELLIGENCE BASED RECONSTRUCTION FOR PHASE CONTRAST MAGNETIC RESONANCE IMAGING

CROSS-REFERENCE TO RELATED APPLICATIONS

This application claims priority from U.S. Provisional Patent Application 63/149,670 filed Feb. 16, 2021, which is incorporated herein by reference.

FIELD OF THE INVENTION

The present invention relates generally to medical imaging. More specifically it relates to phase contrast magnetic resonance imaging.

BACKGROUND OF THE INVENTION

Phase Contrast Magnetic Resonance Imaging (PC-MRI) is widely considered the clinical gold-standard for non-invasive and time-resolved visualization and quantification of blood velocity (cm/s) and flow (mL) throughout the cardiovascular system. Clinically, PC-MRI is used to aid in the diagnosis and treatment of cardiovascular disease, including valvular stenosis (velocity) as well as regurgitation, right/left lung flow splits, and shunts (flow). However, one of the main challenges associated with the technique is the need to minimize the breath hold duration while accommodating the spatiotemporal requirements for accurate and precise measurements of blood velocity and flow.

PC-MRI uses encoding gradients to map the velocity of flowing blood to the phase of the measured complex MR signal. This method requires the acquisition of at least two images with appropriate flow encoding, such that the phase difference of the two flow encoded images eliminates intra-voxel off-resonance effects due to magnetic field inhomogeneity. Furthermore, to mitigate artifacts associated with cardiac and respiratory motion, cardiac ECG triggering is used to acquire data over several heartbeats. This acquisition scheme requires patients to hold their breath for upwards of 20 seconds, which oftentimes can be difficult. Also, conventional PC-MRI requires the scan operator to balance scan duration, artifact mitigation, spatial resolution, temporal resolution, and signal-to-noise ratio (SNR). This balancing act limits the accuracy, precision, and repeatability of the technique.

A wide variety of methods have been proposed to reduce PC-MRI scan times, including non-Cartesian sampling strategies, Parallel Imaging (PI) undersampling, Compressed Sensing (CS), and Low-Rank (LR) matrix recovery. CS is one of the most successful techniques, to date, to decrease PC-MRI scan times by reducing the number of acquired k-space samples via a pseudorandom undersampling scheme. These schemes produce noise-like artifacts that are later removed with iterative reconstruction algorithms that alternately enforce data consistency and denoise based on prior sparse modeling. Specifically for PC-MRI, several studies have exploited the spatiotemporal redundancy of dynamic cardiac images. Nevertheless, the generic assumptions of CS are often unable to accurately describe the complexity of cardiac dynamics, limiting the achievable acceleration and/or reducing the accuracy and precision of clinically important quantitative measures. More recent work has extended the CS sparse representation model to PC-MRI data by directly reconstructing Complex Difference (CD) images rather than traditional phase difference images. CD images are considerably more sparse and could potentially result in increased accuracy and precision at higher acceleration factors.

BRIEF SUMMARY OF THE INVENTION

Herein is disclosed an AI-based PC-MRI reconstruction framework for reconstructing highly accelerated PC-MRI datasets. The method has been shown to 1) reduce scan time, 2) afford the use of higher spatial and/or temporal resolutions, and/or 3) maximize SNR, all of which offer the potential to provide more accurate clinical measurements.

The present AI-based PC-MRI reconstruction framework increases the maximum achievable acceleration while maintaining measurement accuracy and precision. The framework has two main features: 1) a data-driven reconstruction approach based on AI that can be used on multidimensional (2D or 4D PC-MRI) with any data undersampling scheme; and 2) a PC-MRI reconstruction capable of generating both phase difference and complex difference images.

The method employs an unrolled convolutional neural network to perform reconstruction based on an image model directly learned from fully sampled PC-MRI datasets. Furthermore, we combine this with a complex difference image estimation to take advantage of its higher sparsity (higher data compressibility) and improved data recoverability, even at high acceleration factors.

We adapted an AI-based MRI reconstruction framework designed for magnitude cardiac cine MRI to be used with complex-valued, multidimensional PC-MRI images. Our framework is compatible with any data undersampling scheme and can be used to reconstruct velocity information from both 2D and 4D PC-MRI datasets. Furthermore, our technique offers both phase difference and complex difference based reconstructions to improve reconstruction accuracy.

PC-MRI is a diagnostic imaging technique used routinely in clinical practice to assess a wide variety of cardiovascular pathologies. The main application of the present method is to reduce the amount of data that is acquired for PC-MRI, which is a compelling software addition to the major MRI commercial vendors in the field. This reduced acquisition could be leveraged to 1) reduce scan time, 2) afford higher spatial resolution, 3) afford higher temporal resolution, and/or 4) increase SNR, all of which offer the potential to provide more accurate measurements.

The technique has several advantages and improvements over existing methods. Traditional PC-MRI CS reconstruction methods employ iterative algorithms that rely on an assumed sparse representation model of the image. However, these generic models are often unable to accurately describe the complexity of cardiovascular hemodynamics and, thus, limit the maximum attainable acceleration factor. Additionally, CS methods are widely known to suffer from long image reconstruction times.

Our method uses an AI-based reconstruction framework where the sparse model is learned directly from the PC-MRI datasets through the use of a convolutional neural network. Furthermore, we further exploit a specific characteristic of PC-MRI data by directly reconstructing a complex difference image. This complex difference image often presents higher sparsity and, thus, better recoverability at higher acceleration factors. The combination of these two features allows our algorithm to offer a higher acceleration rate (roughly two times improvement) and faster image reconstruction durations (roughly two times improvement) compared to traditional CS techniques.

In one aspect, the invention provides a method for phase-contrast magnetic resonance imaging (PC-MRI), the method comprising: acquiring undersampled PC-MRI data using a magnetic resonance imaging scanner; and reconstructing MRI images from the undersampled PC-MRI data by reconstructing a first flow-encoded image using a first convolutional neural network; reconstructing a complex difference image using a second convolutional neural network; combining the complex difference image and the first flow-encoded image to obtain a second flow-encoded image; and generating a velocity encoded image from the first flow-encoded image and second flow-encoded image using phase difference processing.

Acquiring the undersampled PC-MRI data using the magnetic resonance imaging scanner preferably is performed by acquiring multidimensional (2D or 4D PC-MRI) data. Reconstructing the complex difference image using the second convolutional neural network is preferably performed by inputting to the second convolutional neural network a difference of two portions of the undersampled PC-MRI data having different velocity encodings.

The first convolutional neural network is preferably an unrolled convolutional neural network, and more preferably may be an unrolled deep convolutional neural network. The first convolutional neural network preferably is a DL-ESPIRiT network modified for PC-MRI data. The second convolutional neural network preferably is an unrolled convolutional neural network. The second convolutional neural network preferably is a DL-ESPIRiT network trained with CD PC-MRI data.

BRIEF DESCRIPTION OF THE DRAWINGS

FIG. 3A shows accuracy (RMSE) for pixel velocity differences expressed as a % of VENC.

FIG. 3B shows precision (95%-CIs) for pixel velocity differences expressed as a % of VENC.

FIG. 3C shows accuracy (RMSE) for peak velocity differences expressed as a % difference compared to Full.

FIG. 3D shows precision (95%-CIs) for peak velocity differences expressed as a % difference compared to Full.

DETAILED DESCRIPTION OF THE INVENTION

Herein is disclosed a deep learning-based reconstruction framework for highly accelerated 2D PC-MRI data that allows accurate and precise quantitative measurements. In one embodiment, a modified DL-ESPIRiT reconstruction framework for 2D PC-MRI includes an unrolled neural network architecture and a direct Complex Difference (CD) estimation approach (CD-DL). In one illustrative implementation, the CD-DL network is trained on 155 fully-sampled 2D PC-MRI pediatric clinical datasets. Fully-sampled data (n=29) is retrospectively undersampled (R=6-11) and reconstructed using CD-DL and a state-of-the-art parallel imaging and compressed sensing method (PICS). Estimates of peak velocity and total flow are compared between the fully-sampled, PICS, and CD-DL data to determine the highest acceleration rate that provides accuracy and precision within 15%. The retrospective analysis shows that 9× accelerated 2D PC-MRI images reconstructed with the proposed CD-DL framework provides higher accuracy (bias) and precision (95% confidence intervals) for measurements of peak velocity (3.9 (−11.0, 4.9)% vs. 2.8 (−2.9, 4.5)%) and total flow (1.8 (−3.9, 3.4)% vs. 2.9 (−7.1, 6.9)%) compared to PICS. The CD-DL framework produces quantitative measurements of 2D PC-MRI peak velocity and total flow for up to 9× acceleration with accuracy and precision within ±5%.

In one embodiment of the invention, a method is provided that uses a DL-based reconstruction framework for highly accelerated 2D PC-MRI data. The approach extends an existing DL-ESPIRiT reconstruction framework developed for cardiac cine MRI and adapts it for 2D PC-MRI datasets using a direct CD reconstruction approach, denoted CD-DL. We define the maximum achievable acceleration for the proposed CD-DL reconstruction framework for retrospectively undersampled 2D PC-MRI data while maintaining clinically relevant measures of peak velocity and total flow within 15% when compared to fully-sampled datasets. We also determine to what extent the present CD-DL reconstruction framework outperforms a conventional parallel imaging and compressed sensing reconstruction (PICS) framework in terms of peak velocity and total flow accuracy and precision.

Network Architecture

Figure 1A:
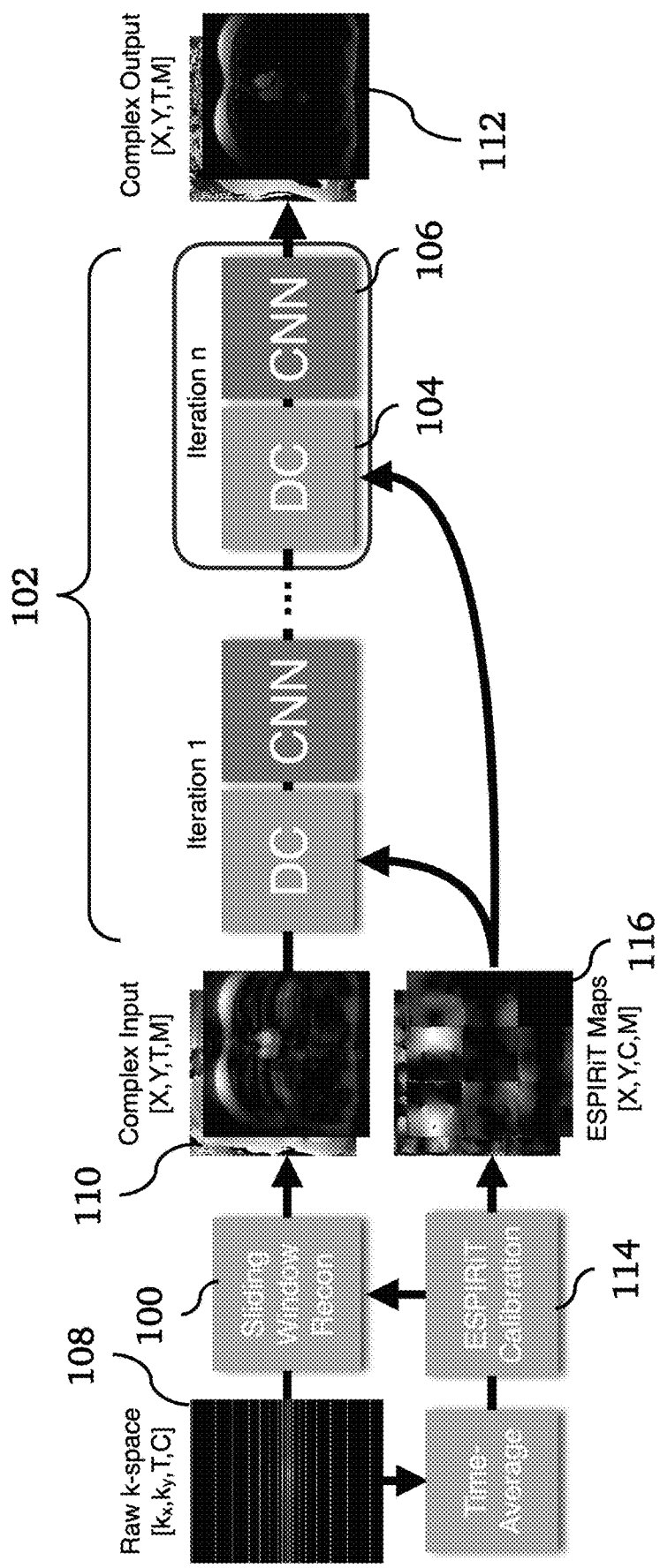
FIG. 1A is an illustration of a DL-ESPIRiT reconstruction pipeline that adopts the Neural Proximal Gradient Descent architecture (NPGD), according to an embodiment of the invention.

A DL-ESPIRiT reconstruction pipeline adopts the Neural Proximal Gradient Descent architecture (NPGD), as depicted in FIG. 1A. This DL-ESPIRiT reconstruction pipeline uses an initial reconstruction comprised of a sliding window 100 with temporal window size of five and an unrolled network architecture 102 with n steps that iteratively alternate between a Data Consistency (DC) update 104 and a CNN-based denoising step 106. The raw k-space data 108 from the MRI scanner acquisition is applied to the sliding window reconstruction 100 to produce complex input 110 to the unrolled network 102 which generates complex output 112.

An extended coil sensitivity model based on ESPIRiT 114 generates two sets of sensitivity maps 116 used by the DC updates 104 to provide robustness against SENSE-related field-of-view (FOV) limitations.

In the data 108, 116 $k_x$ and $k_y$ represent the row and column dimensions in k-space, T is the time dimension, C is the coil dimension, and M represents the set of sensitivity maps.

Figure 1B:
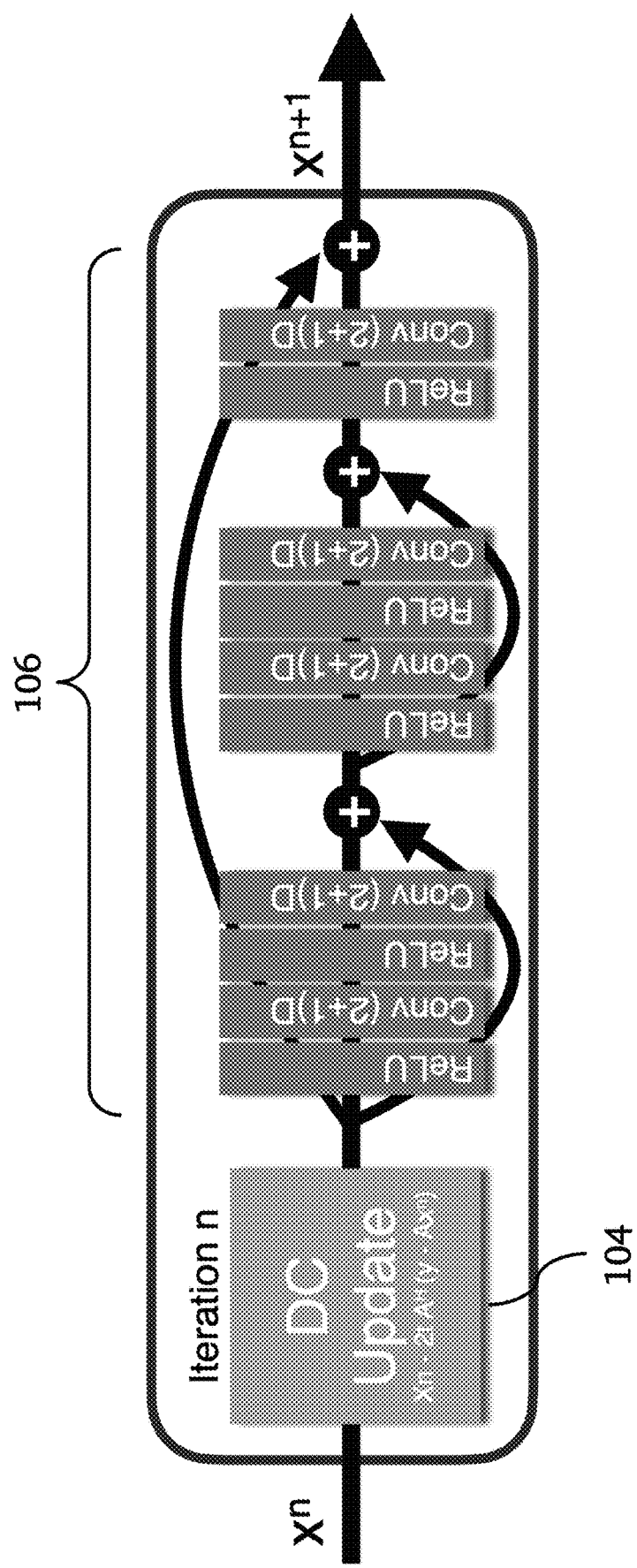
FIG. 1B illustrates details of DC and CNN blocks of the unrolled network in FIG. 1A, according to an embodiment of the invention.

The network iteratively alternates between enforcing Data Consistency (DC) and denoising based on a data-driven model parameterized by a CNN. FIG. 1B further details the DC block 104 and CNN 106 of each iteration step of the unrolled network 102. The DC block 104 applies a gradient descent step enforcing data consistency between the resulting image and the acquired k-space data. Each CNN block 106 is a fully convolutional residual network (ResNet) with (2+1)D convolutions. The CNN has a Rectified Linear Unit (ReLU) pre-activation layer and a 2D spatial and 1D temporal (2+1)D convolutional layer.

Figure 1C:
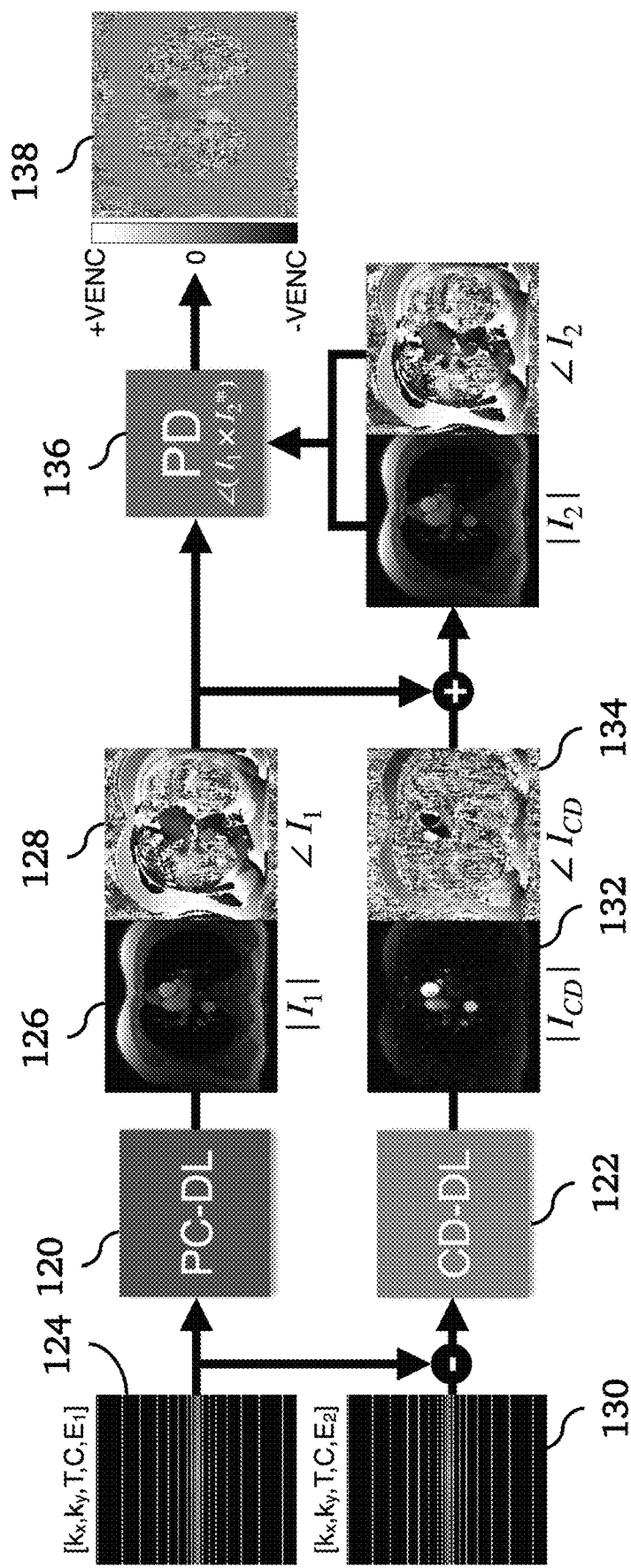
FIG. 1C illustrates CD-DL PC-MRI reconstruction processing pipelines combined to generate velocity images from k-space data from two velocity encodings, according to an embodiment of the invention.

Two networks were trained to comprise the CD-DL PC-MRI reconstruction pipelines, as shown in FIG. 1C.

PC-MRI sequences involve the acquisition of two velocity encodings. When PC-MRI sequences are used in an MRI scan, two sets of raw k-space data 124 and 130 are acquired, one for each velocity encoding.

First, we trained a DL-ESPIRiT network 120 that was modified for PC-MRI data. This network is denoted as PC-DL and reconstructs from k-space data 124 the magnitude 126 and phase 128 components of image $I_1$ which corresponds to the first velocity encoding.

Second, we used a DL-ESPIRiT network 122, denoted CD-DL, which uses the k-space data 124 and 130 from both velocity encodings to reconstruct a CD image, $I_{CD}$, computed from the difference between k-space data 124 and 130. Image $I_{CD}$ has both a magnitude 132 and phase 134 component. The CD-DL network 122 takes advantage of the higher sparsity of the CD image relative to the individual velocity-encoded images. In the data 124, 130 $k_x$ and $k_y$ represent the row and column dimensions in k-space, T is the time dimension, C is the coil dimension, and $E_1$ and $E_2$ represent the two flow (or velocity) encoded images.

The final velocity images 138 are obtained using the output of the PC-DL network 120 and the CD-DL network 122 through the use of phase difference processing 136, which computes $\angle(I_1 I_2^*)$ from the resulting $I_1$ and $I_2 = I_{CD} + I_1$.

Data Acquisition

Conventional 2D PC-MRI clinical data is commonly acquired using 2× in-plane PI. To avoid potential errors introduced by the PI reconstruction, we opted to use fully-sampled single slice 2D PC-MRI datasets (n=194), without PI, to serve as the ground truth data for training our DL reconstruction networks. Clinical pediatric, fully-sampled datasets were retrospectively obtained from December 2017 to October 2020. All imaging was performed on either a 1.5 T (n=24) or 3.0 T (n=170) MRI system (GE Healthcare, Waukesha, Wis., USA) using a commercial ECG-gated spoiled gradient echo sequence. Imaging territories included the aorta (n=83), pulmonary artery (n=60), branch pulmonary arteries (n=14), mitral valve (n=10), tricuspid valve (n=6), and various other vessels (n=21).

Training

The 194 ground truth fully-sampled k-space datasets were divided into three groups for training (155 patients: median age, 14.2 years; interquartile range (IQR), 6.3 years; 6,200 images, 80%), validation (10 patients: median age, 16.0 years; IQR, 9.5 years; 400 images, 5%), and testing (29 patients: median age, 17.4 years; IQR, 6.5 years; 1,160 images, 15%). The number of training datasets were further increased with data augmentation using random flipping, translations, cropping, and temporal interpolation as described in the original DL-ESPIRiT implementation in addition to phase augmentation. Variable-density undersampling masks with 6-11× acceleration and 25% partial Fourier across the $k_y$-t plane were randomly generated and applied on-the-fly to each dataset during training.

Training and inference pipelines were implemented using TensorFlow. Networks were trained with a batch size of one using the ADAM optimizer with hyperparameters $\beta_1$=0.9, $\beta_2$=0.999, $\epsilon$=$10^{-8}$, and an initial learning rate of $10^{-3}$, which was reduced to $10^{-4}$ after 120,000 steps until convergence was reached at 220,000 steps. Multiple CD-DL networks were trained, but the optimal networks architecture comprised of ten NPGD iterations, two ResNet per iteration, and 96 feature maps per convolutional layer (5,191,680 total learnable parameters). All networks trained for ≈108 hours (two 24 GB NVIDIA Titan RTX video cards with an NVLink Bridge, two 16 core CPUs at 2667 MHz, 1 TB RAM, and eight 3.8 GB SSDs).

Quantitative Flow Metrics

For each dataset, a single ROI was contoured around the lumen of the vessel of interest within the magnitude images in Horos. The ROIs and DICOMs were then imported into MATLAB (MathWorks, Natick, Mass., USA). Peak velocity (cm/s) was calculated by finding the as the top 5% of all pixels contained within the ROIs. Total flow (mL) was calculated as the mean ROI velocity (cm/s) multiplied by the area of the ROI (cm²) integrated over the cardiac cycle.

Retrospective Evaluation

Conventional magnitude-focused DL networks use image similarity metrics, which may be ineffective for assessing accuracy in PC-MRI datasets. Instead, we specified our own metrics to quantify accuracy and precision. Herein we compare the accuracy of the tested reconstruction methods to that of the fully-sampled data using metrics such as median difference and root-mean-squared error (RMSE). Additionally, we compare the precision of the tested reconstruction methods to that of the fully-sampled data by computing the upper and lower 95% confidence intervals (95%-CIs). We defined 15% accuracy and precision thresholds, relative to the fully-sampled data, for both peak velocity and total flow. We used these criteria to determine the maximum acceleration rate for each reconstruction method that maintained the desired accuracy and precision for peak velocity and total flow.

To assess reconstruction performance we compared fully-sampled with CD-DL and a standard PICS reconstruction method. PICS uses l1-ESPIRiT with spatial and temporal total variation (TV) regularization. Regularization strengths for spatial and temporal TV priors were empirically determined to be 0.002 and 0.01, respectively, based on our pre-tuning of the regularization parameters. The PICS problem was solved using the Alternating Direction Method of Multipliers algorithm with 200 inner loop iterations. We performed the reconstruction using the Berkeley Advanced Reconstruction Toolbox (BART, v0.4.04) implementation with GPU acceleration. Reconstruction times for the fully-sampled, PICS, and CD-DL methods were 2.0±0.3 s, 7.5±1.4 s, and 12.0±1.6 s, respectively.

We compared pixel-by-pixel velocity differences, peak velocity error, and total flow error for integer acceleration rates ranging from 6× to 11× to determine which reconstruction method provided the greatest acceleration factor while maintaining a RMSE and 95%-CIs within 15% of fully-sampled. We also compared each method to fully-sampled using linear regression and reported the goodness of fit metric ($R^2$), slope, intercept, RMSE, and 95%-CIs.

Static tissue interpolation was performed on all test datasets (n=29) to characterize the impact of our reconstruction networks on background phase offsets. The reconstructed DICOMs were masked using a 6% signal intensity threshold to isolate regions of flow and static tissue in the magnitude and phase images. A two-degree polynomial was then fit to the static tissue mask and used to estimate the background phase offsets within the vessel region-of-interest (ROI). Next, we estimated the difference in background phase offsets on a pixel-by-pixel basis within static tissue and the vessel ROI for fully-sampled vs. PICS and fully-sampled vs. CD-DL. We conducted a histogram analysis of pixel velocity, showing the offset median as well as the 95%-CIs. Background phase offsets in the fully-sampled data were assumed to be exclusively from eddy currents while deviations arising from the PICS or CD-DL datasets were assumed to be due to the previously reported reconstruction-induced background phase offsets, which may arise due to the non-linear nature of CS and DL reconstruction methods.

Results

Figures 2A, 2B:
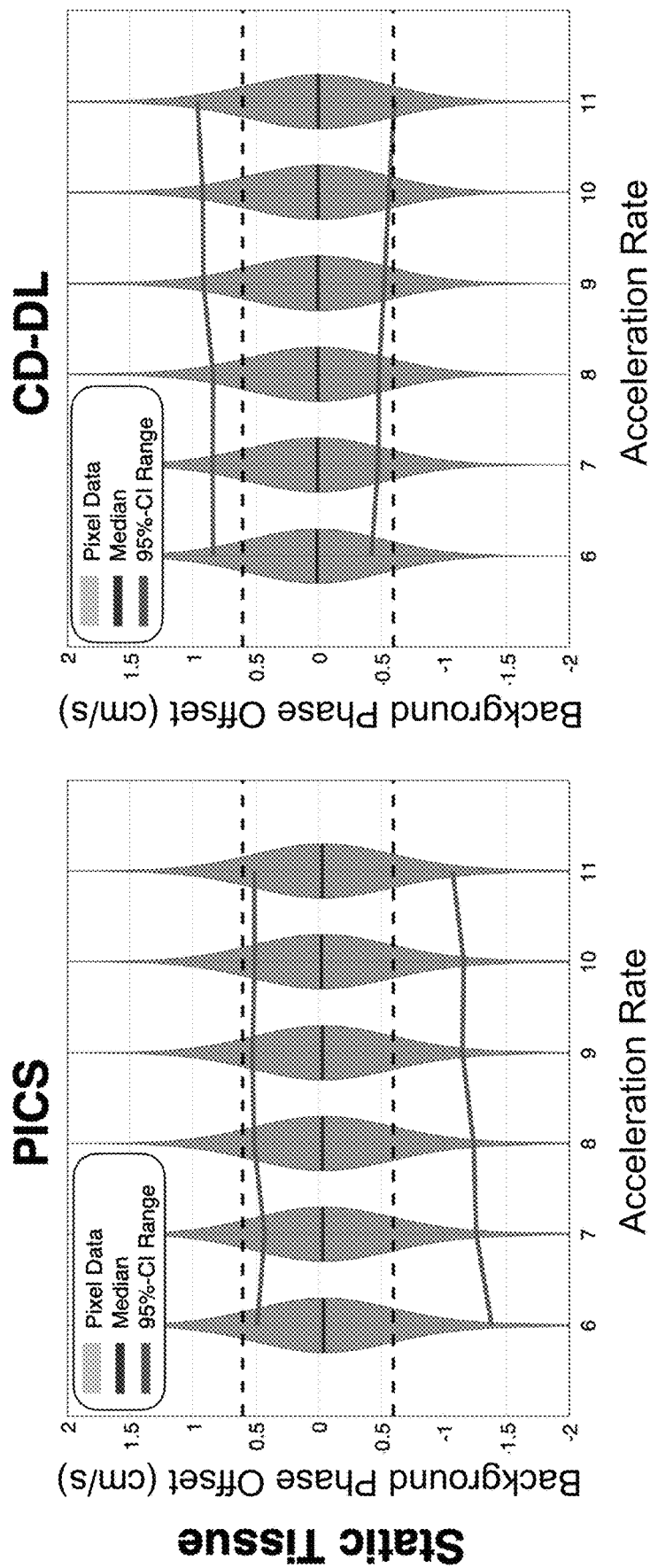
FIG. 2A is a histogram illustrating the magnitude of the pixel background phase offsets (cm/s) from differences within static background tissue for PICS compared to fully-sampled, as a function of acceleration rate.
FIG. 2B is a histogram illustrating the magnitude of the pixel background phase offsets (cm/s) from differences within static background tissue for CD-DL compared to fully-sampled, as a function of acceleration rate.
Figures 2C, 2D:
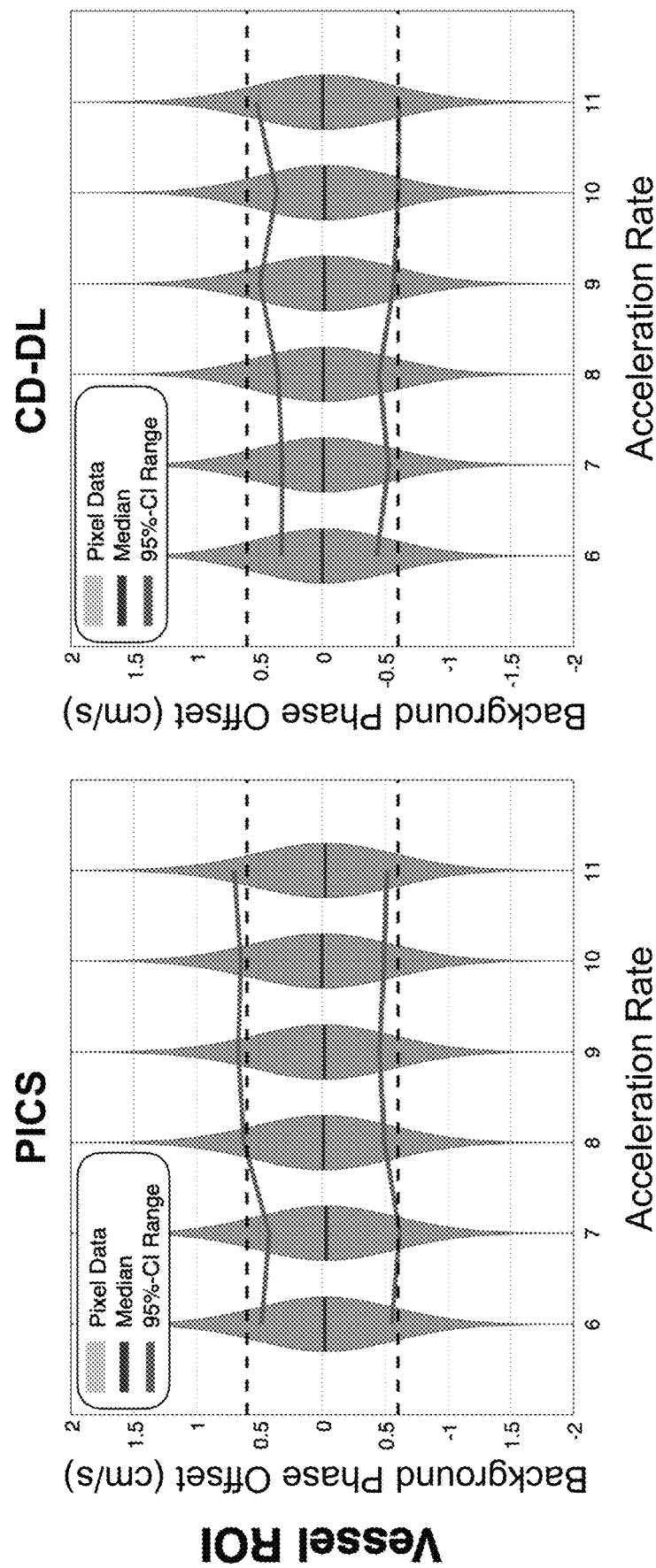
FIG. 2C is a histogram illustrating the magnitude of the pixel background phase offsets (cm/s) from differences inside the vessel ROIs for PICS compared to fully-sampled, as a function of acceleration rate.
FIG. 2D is a histogram illustrating the magnitude of the pixel background phase offsets (cm/s) from differences inside the vessel ROIs for CD-DL compared to fully-sampled, as a function of acceleration rate.

Owing to the importance of background phase errors in PC-MRI, we examined whether each reconstruction approach introduced a bias to the background phase, which would be especially difficult to correct if it differentially impacted static and flowing spins. FIG. 2A-B show histograms illustrating the magnitude of the pixel background phase offsets (cm/s) from differences within static background tissue (shown in FIGS. 2A-B) and inside the vessel ROIs (shown in FIGS. 2C-D) for PICS and CD-DL compared to fully-sampled, as a function of acceleration rate. The accuracy is defined by the median and the precision by the 95%-CIs. The horizontal dashed lines represent the clinically acceptable threshold of ±0.6 cm/s. Accuracy is consistent across all reconstruction techniques while CD-DL shows higher precision compared to PICS. The present CD-DL reconstruction framework showed increased background phase offsets relative to fully-sampled, but importantly these offsets were consistently predictable, using static tissue interpolation, across the image (static tissue vs. ROI vessel). Furthermore, our CD-DL method showed narrower 95%-CIs in background phase offsets compared to conventional PICS.

Figure 3F:
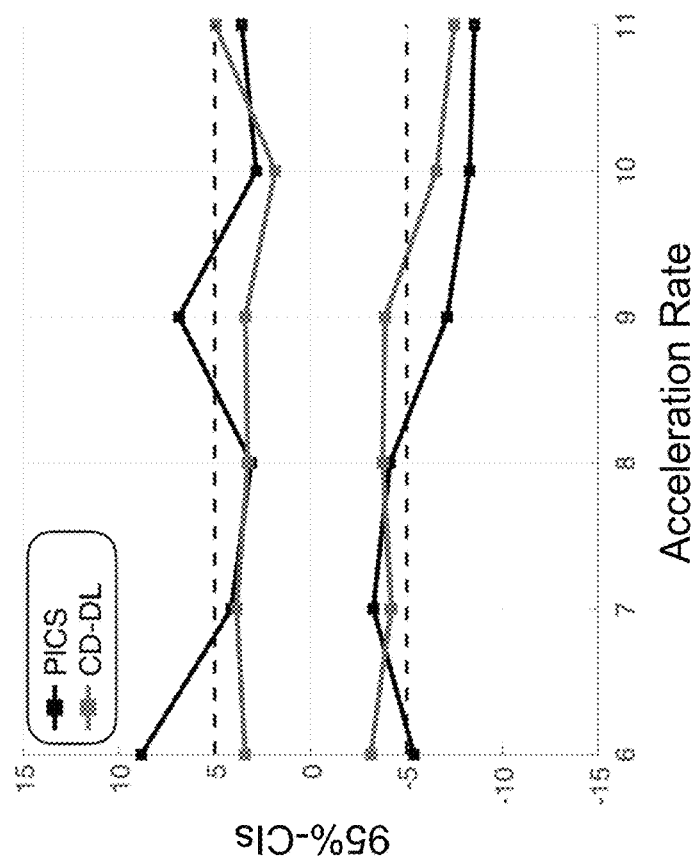
FIG. 3F shows precision (95%-CIs) for total flow differences expressed as a % difference compared to Full.
Figure 3E:
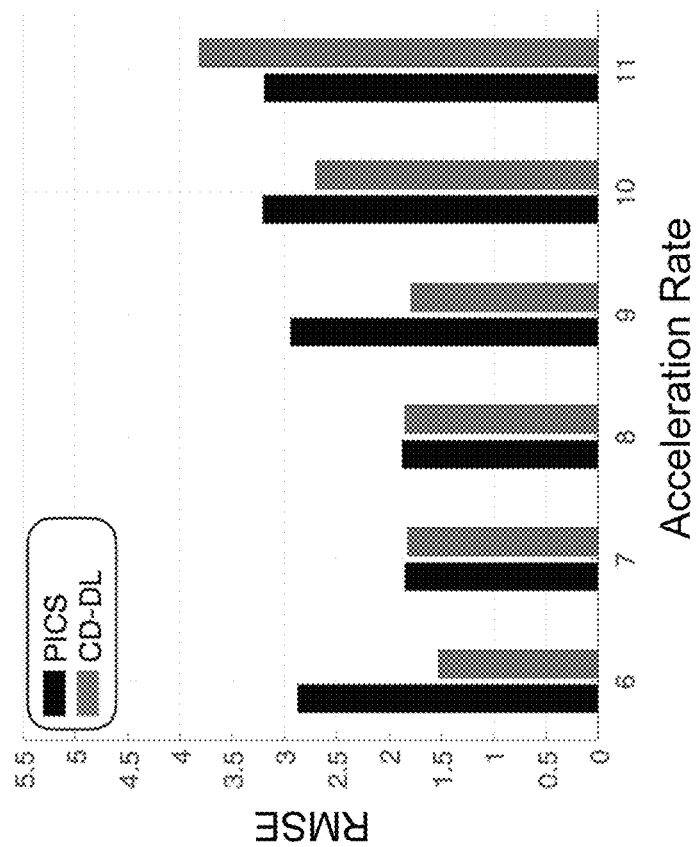
FIG. 3E shows accuracy (RMSE) for total flow differences expressed as a % difference compared to Full.

We examined a range of acceleration rates to analyze the impact of our CD-DL on the accuracy and precision of peak velocity and total flow measurements. FIGS. 3A-F show a summary of the quantitative flow metrics for PICS and CD-DL compared to fully-sampled as a function of acceleration rate. FIGS. 3A-B show accuracy (RMSE) and precision (95%-CIs), respectively, for pixel velocity differences expressed as a % of VENC. FIGS. 3C-D show accuracy (RMSE) and precision (95%-CIs), respectively, for peak velocity differences expressed as a % difference compared to Full. FIGS. 3E-F show accuracy (RMSE) and precision (95%-CIs), respectively, for total flow differences expressed as a % difference compared to Full. The accuracy is analyzed by plotting the RMSE (bar graphs) while the precision is analyzed by plotting the 95%-CIs (lines). The CD-DL method meets the ±5% accuracy threshold for all tested acceleration rates and meets the ±5% precision threshold for acceleration rates up to 9×, whereas PICS shows inconsistent precision across all acceleration rates. Note, the 95%-CIs are plotted with connecting lines between successive integer acceleration rates to improve the visualization of the data.

For 6-10× acceleration factors, the RMSE was lower for CD-DL compared to PICS, representing increased accuracy. Similarly, the 95%-CIs are narrower for CD-DL compared to PICS, indicating increased precision. FIGS. 3A-F highlight that CD-DL limits the error in peak velocity and total flow accuracy and precision less than 5% for accelerations rates up to 9×. A summary of the quantitative flow metrics (mean ROI velocity, peak velocity, and total flow) across all patients (n=29) comparing fully-sampled and 9× accelerated PICS and CD-DL is shown in Table 2. The analysis includes the RMSE (accuracy) and 95%-CIs (precision) expressed as a % of the VENC for mean ROI velocity and as a % for peak velocity and total flow. PICS falls outside of our 15% precision threshold for peak velocity and total flow, while CD-DL is within both the accuracy and precision threshold for all metrics.

Figure 4A:
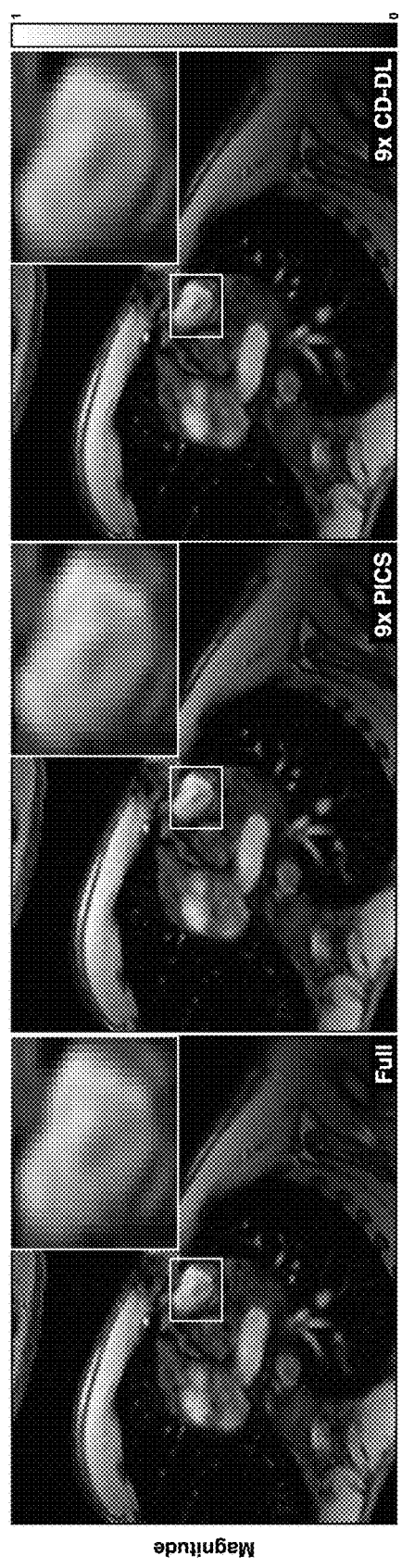
FIG. 4A shows magnitude images from a single representative patient dataset for fully-sampled and 9× accelerated data reconstructed using PICS and CD-DL.
Figure 4B:
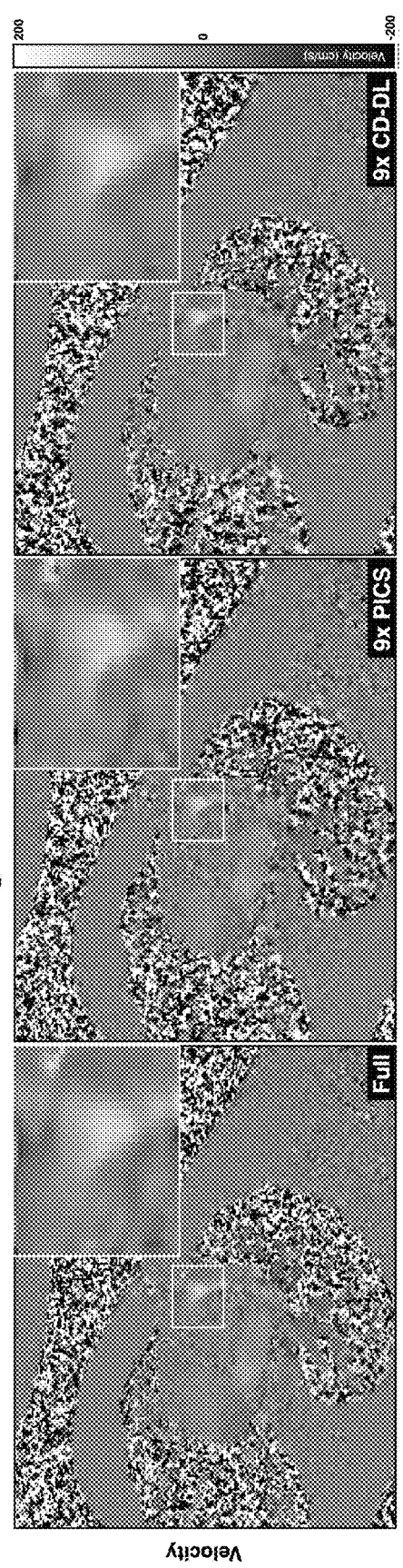
FIG. 4B shows velocity images from a single representative patient dataset for fully-sampled and 9× accelerated data reconstructed using PICS and CD-DL.
Figure 4C:
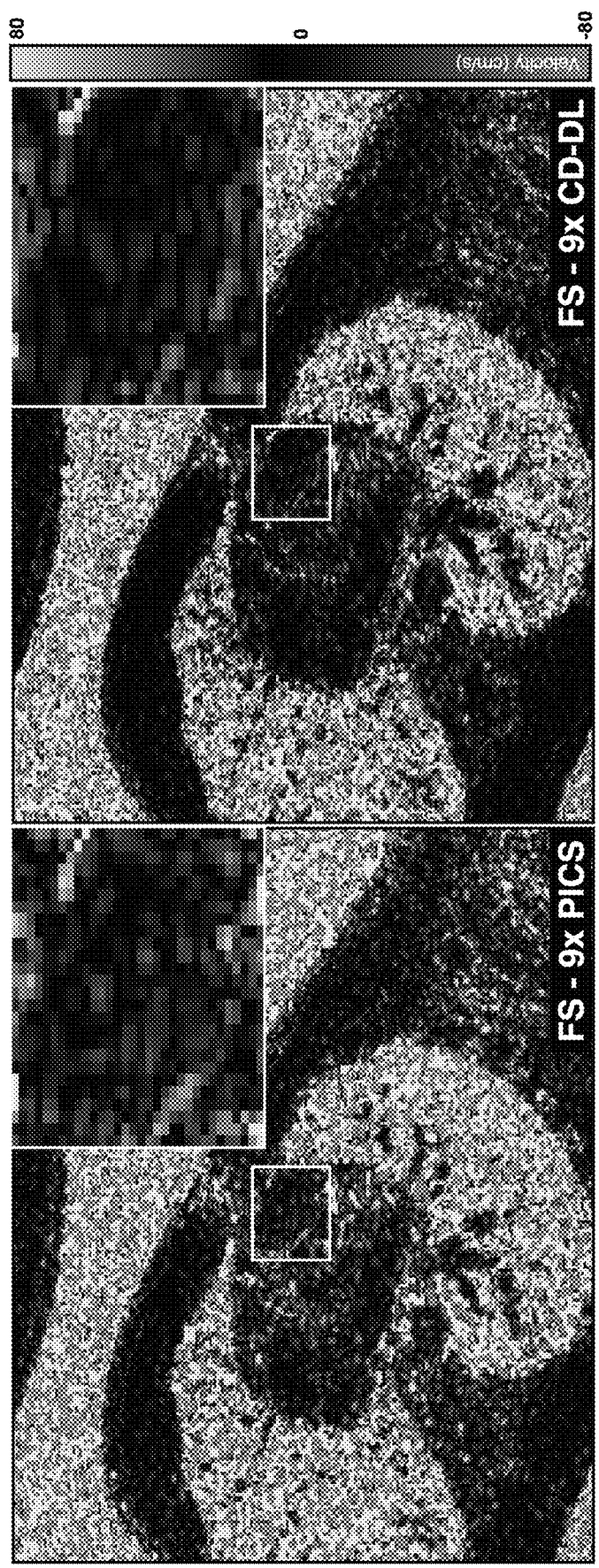
FIG. 4C shows velocity difference images from a single representative patient dataset for fully-sampled and 9× accelerated data reconstructed using PICS and CD-DL.

FIGS. 4A-C show images from a single representative patient dataset highlighting the magnitude (FIG. 4A), velocity (FIG. 4B), and velocity difference (FIG. 4C) images for fully-sampled and 9× accelerated data reconstructed using PICS and CD-DL. Qualitatively the magnitude and velocity images appear similar for all reconstruction methods, but the velocity difference images comparing fully-sampled and 9×CD-DL show reduced velocity errors compared to 9×PICS. Pixel-by-pixel difference images highlight that CD-DL offers reduced velocity errors (more black pixels) compared to PICS.

Figure 5A:
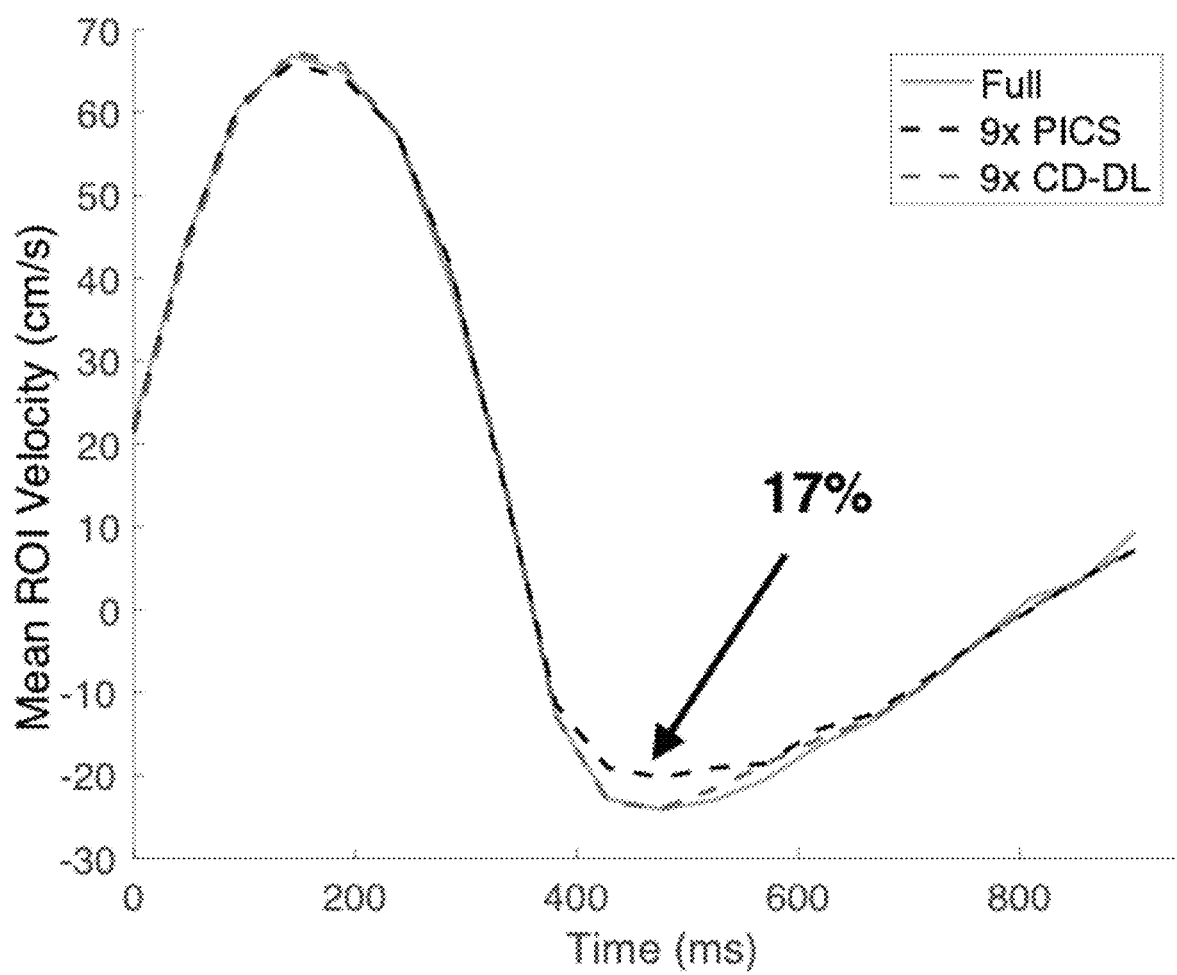
FIG. 5A is a graph of mean ROI velocity (cm/s) vs. time for fully-sampled (Full) and 9× undersampled data reconstructed using PICS and CD-DL.
Figure 5B:
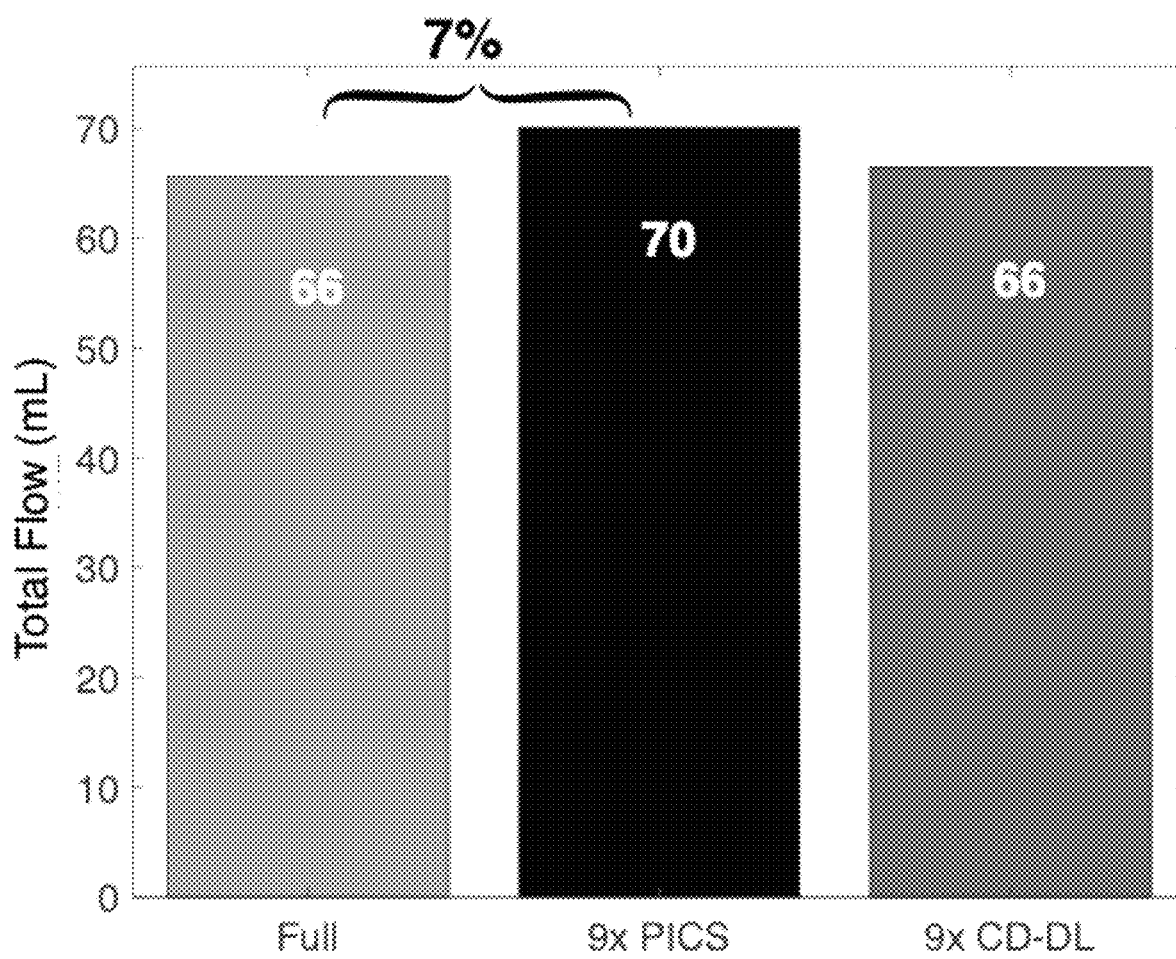
FIG. 5B is a graph of total flow (mL) for fully-sampled (Full) and 9× undersampled data reconstructed using PICS and CD-DL.
Figure 5C:
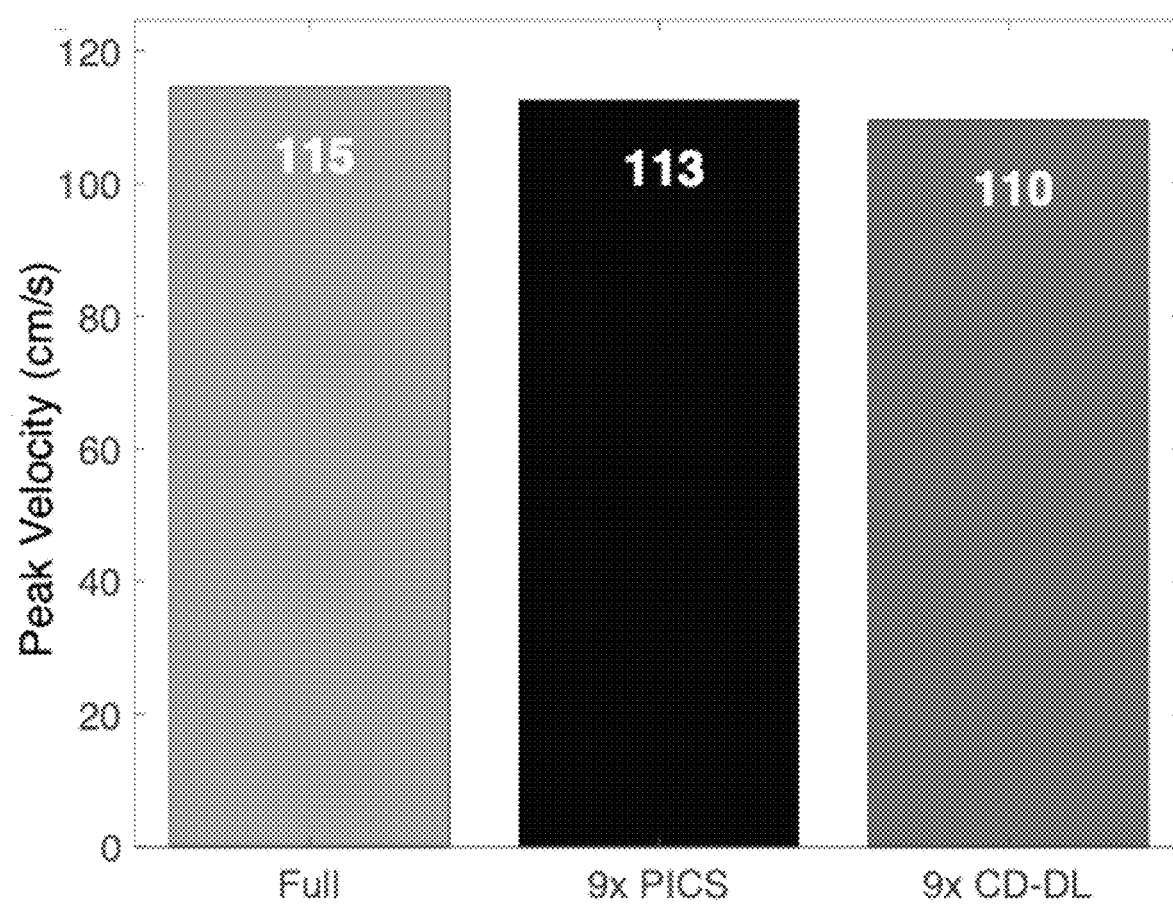
FIG. 5C is a graph of peak velocity (cm/s) for fully-sampled (Full) and 9× undersampled data reconstructed using PICS and CD-DL.

These reduced errors lead to increased accuracy in both mean ROI velocity and total flow estimates. FIGS. 5A-C show the quantitative flow metrics for the same exemplary representative case as highlighted in FIGS. 4A-C. FIG. 5A is a graph of mean ROI velocity (cm/s) vs. time for fully-sampled (Full) and 9× undersampled data reconstructed using PICS and CD-DL. FIG. 5B is a graph of total flow (mL) for fully-sampled (Full) and 9× undersampled data reconstructed using PICS and CD-DL. FIG. 5C is a graph of peak velocity (cm/s) for fully-sampled (Full) and 9× undersampled data reconstructed using PICS and CD-DL. The mean ROI velocity curves show differences up to 17% for PICS compared to Full. Similarly, PICS overestimates total flow by 7%. CD-DL shows increased accuracy, with up to 6% errors in mean ROI velocity and 1.2% overestimation of total flow. Peak velocity accuracy is similar between PICS and CD-DL.

Figure 6:
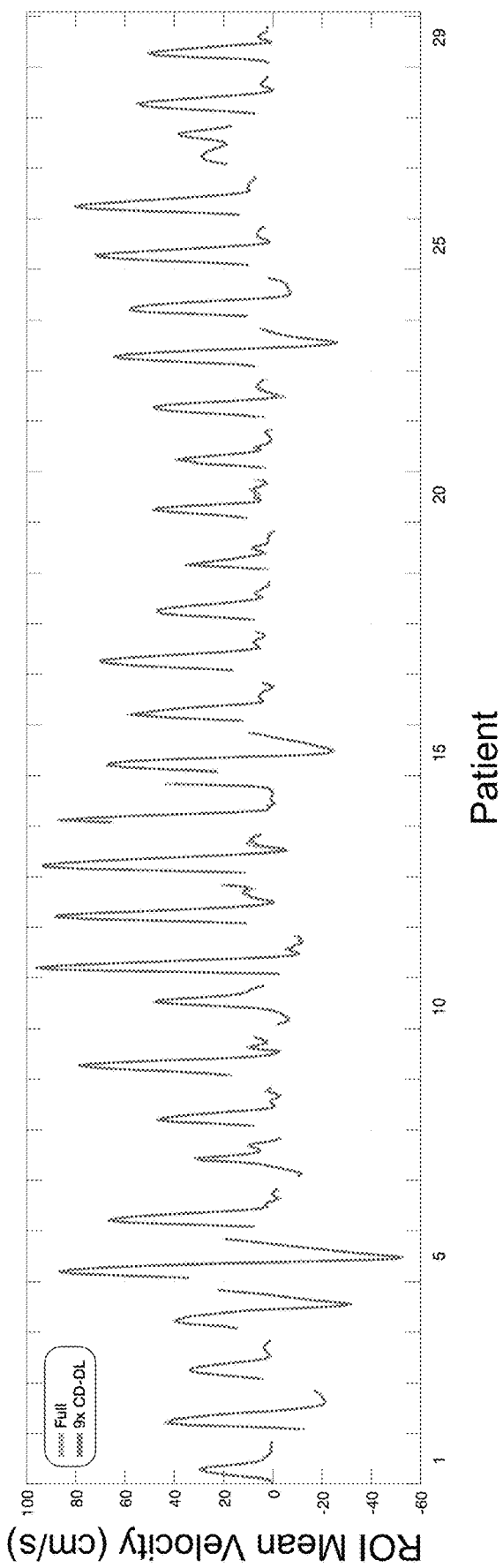
FIG. 6 is a graph showing a qualitative comparison between fully-sampled and 9×CD-DL of the measured mean ROI velocity (cm/s) over the cardiac cycle plotted for different patients.

PICS reconstruction of the velocity image results in an overestimation of the mean ROI velocity by as much as 17% (FIG. 5A). This inaccuracy leads to a 7% error in total flow estimation, which is outside the ±5% error threshold (FIG. 5B). On the other hand, CD-DL shows higher accuracy with only a 1.2% and 0.13% overestimation of total flow and peak velocity, respectively. In addition, a qualitative comparison can be seen for the worst-case patient in Supporting Information S2 along with the corresponding quantitative flow metrics in Supporting Information S3. FIG. 6 shows a qualitative comparison of fully-sampled vs. 9×CD-DL for the measured mean ROI velocity over the cardiac cycle plotted for every patient (n=29).

FIG. 6 is a graph showing a qualitative comparison between fully-sampled and 9×CD-DL of the measured mean ROI velocity over the cardiac cycle plotted for every patient (n=29). The sparse regions represent excellent agreement between fully-sampled and 9×CD-DL.

Figure 7A:
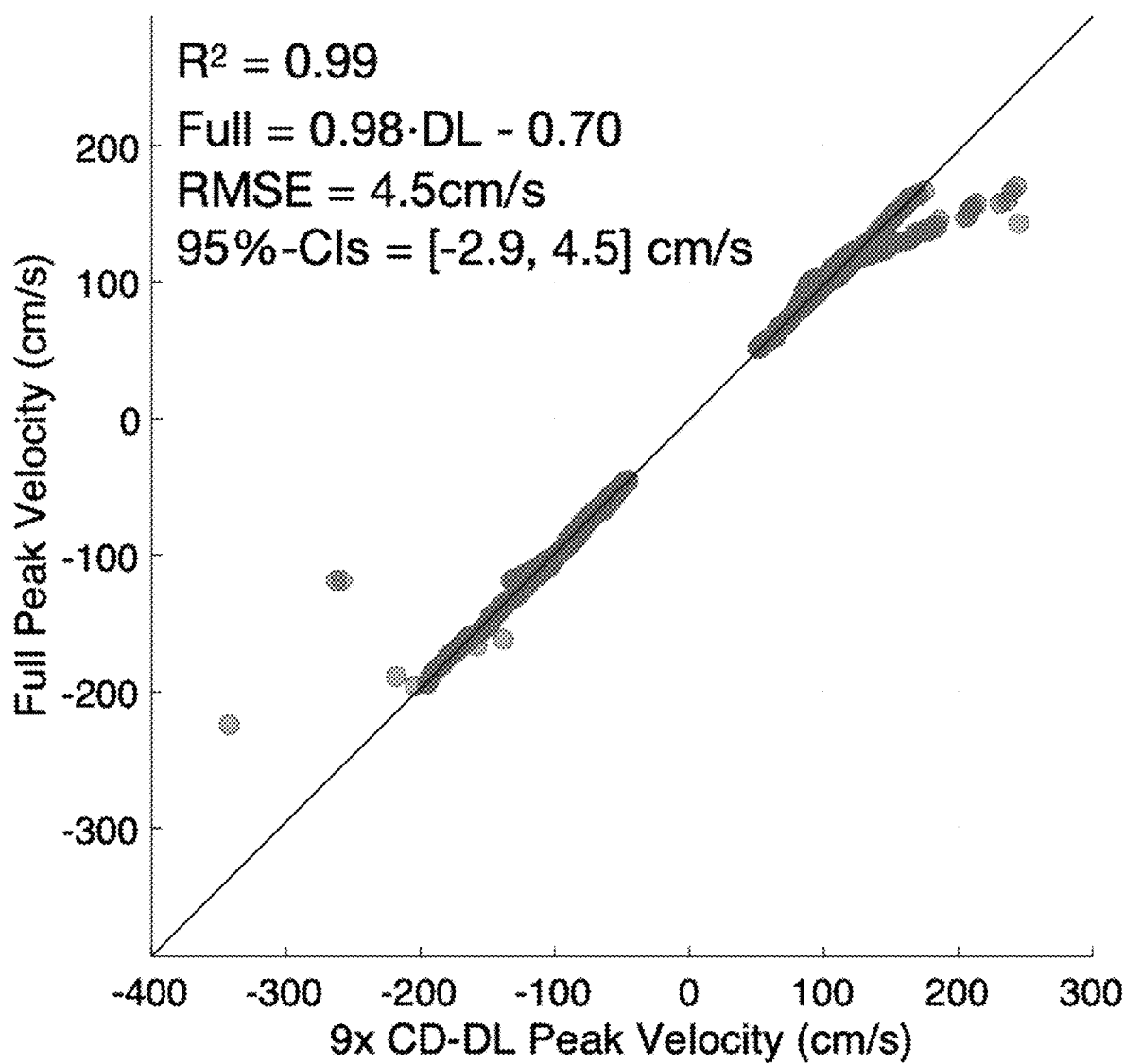
FIG. 7A is a graph showing linear regression analysis for peak velocity (cm/s) between fully-sampled (Full) and CD-DL at 9× acceleration.
Figure 7B:
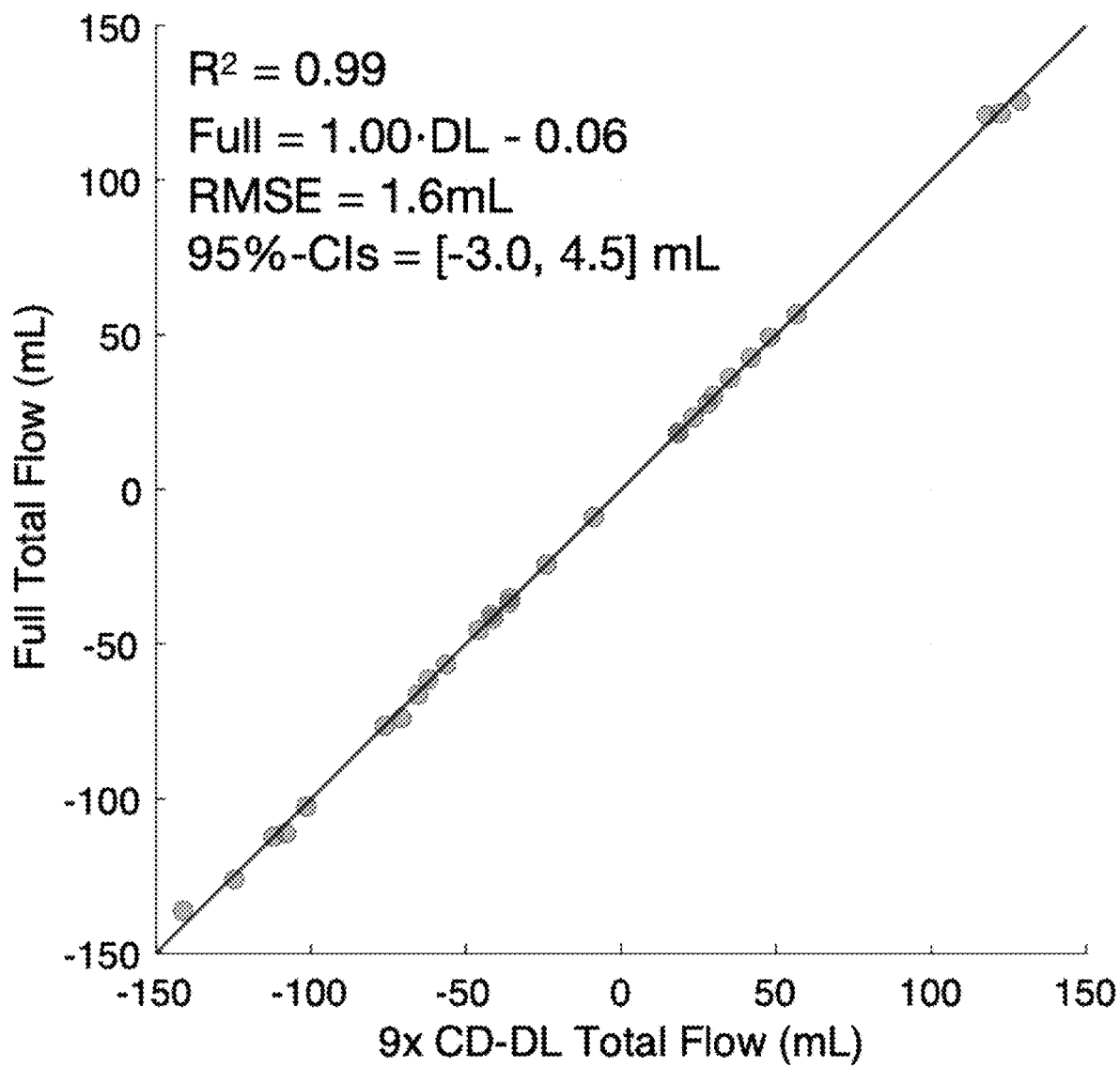
FIG. 7B is a graph showing linear regression analysis for total flow (mL) between fully-sampled (Full) and CD-DL at 9× acceleration.

FIGS. 7A-B are graphs showing linear regression analysis for peak velocity (cm/s) and total flow (mL), respectively, between fully-sampled (Full) and CD-DL at 9× acceleration (n=29). The measurement accuracy and precision for CD-DL is within our ±5% limit with RMSE values of 4.5 cm/s for peak velocity and 1.6 mL for total flow and 95%-CIs of [−2.9, 4.5] cm/s for peak velocity and [−3.0, 4.5] mL for total flow. FIGS. 7A-B show excellent agreement for peak velocity and total flow between fully-sampled and 9× accelerated CD-DL for all patients. The $R^2$ values are 0.99 for peak velocity and total flow. The fitted slopes are 0.98 for peak velocity and 1.00 for total flow. The y-intercepts are −0.7 cm/s for peak velocity and −0.06 mL for total flow.

DISCUSSION

CD-DL was trained on 155 2D PC-MRI datasets and used to reconstruct 29 retrospectively undersampled datasets to determine the maximum acceleration rate that could be achieved while maintaining accurate and precise measurements of peak velocity and total flow. CD-DL showed increased accuracy and precision when compared to PICS and afforded acceleration rates up to 9× while maintaining ≤5% error in both accuracy and precision compared to fully-sampled datasets.

Our CD-DL reconstruction framework offers up to 9× acceleration without compromising important clinical measures of peak velocity and total flow. It is noted that the use of two separately trained networks takes time for both training and inference. During inference, the time needed to load the second network makes CD-DL reconstruction time longer than PICS. This reconstruction time, however, is unlikely to be a bottleneck for clinical workflow (less than 13 seconds). It is also noted that, although our performance metrics were based on hemodynamic blood flow parameters derived from the phase images, our networks in the example discussed above were trained using a generic l1 loss for magnitude-focused image reconstruction. Other embodiments of the invention may use tailored training losses that combine optimization directly on the phase images and masking of the blood vessels of interest. It is also noted that our networks were trained over a range of acceleration factors to explore which acceleration rates could meet our accuracy and precision error thresholds. These variable-density undersampling masks were computed using a random seed as input, resulting in slightly different undersampling masks even for fixed acceleration rates. Although we used the same undersampling masks when comparing across reconstruction methods (i.e., PICS vs. CD-DL), in other embodiments it may be preferable to identify an optimal undersampling mask for a given acceleration rate and matrix size and use that mask for training and testing of prospectively acquired data. This strategy could potentially lead to higher acceleration rates and/or increased accuracy and precision.

CONCLUSION

We have disclosed herein a deep learning-based reconstruction for accurate quantitative measurements of highly accelerated 2D PC-MRI data. We modified a previously described DL-ESPIRiT reconstruction framework to encompass two velocity encodings with CD estimation to improve sparse modeling and reconstruction accuracy. CD-DL produces quantitative measurements of 2D PC-MRI peak velocity and total flow with ≤5% error in both accuracy and precision for up to 9× acceleration while also outperforming conventional PICS.

TABLE 1

Patient demographics and 2D PC-MRI imaging parameters from the retrospective evaluation (n = 194). Data reported as mean ± standard deviation.

|  | Retrospective Evaluation |
| --- | --- |
| Sex (male/female) | 37/28 |
| Age (years) | 15.0 ± 6.3 |
| Weight (kg) | 55.7 ± 25.4 |
| Heart Rate (beats/minute) | 76.6 ± 12.0 |
| Scan Time (s) | 21.1 ± 19.6 |
| TE (ms) | 2.0 ± 0.2 |
| TR (ms) | 5.3 ± 0.3 |
| Temporal Resolution (ms) | 41.7 ± 6.1 |
| VENC (cm/s) | 270 ± 109 |
| Flip Angle (degrees) | 22 ± 3.9 |
| FOV (mm) | 290 ± 32 × 285 ± 35 |
| Pixel Size (mm) | 1.4 ± 0.3 × 1.7 ± 0.3 |
| Slice Thickness (mm) | 9.1 ± 1.6 |
| Bandwidth (kHz) | 62.5 ± 0.0 |

TABLE 2

Quantitative summary of the flow metrics from the retrospective evaluation across all patients (n = 29) comparing fully-sampled with 9× accelerated PICS and CD-DL expressed as the RMSE (lower and upper 95%-CIs) for mean ROI velocity, peak velocity, and total flow.

|  | PICS | CD-DL |
| --- | --- | --- |
| Mean ROI Velocity (% of VENC) | 0.7 (−1.8, 1.5) | 0.5 (−1.1, 1.1) |
| Peak Velocity (% of Full) | 3.9 (−11.0, 4.9) | 2.8 (−2.9, 4.5) |
| Total Flow (% of Full) | 2.9 (−7.1, 6.9) | 1.8 (−3.9, 3.4) |

The invention claimed is:

1. A method for phase-contrast magnetic resonance imaging (PC-MRI), the method comprising:
   (a) acquiring undersampled PC-MRI data using a magnetic resonance imaging scanner; and
   (b) reconstructing MRI images from the undersampled PC-MRI data by
      i. reconstructing a first flow-encoded image using a first convolutional neural network;
      ii. reconstructing a complex difference image using a second convolutional neural network;

iii. combining the complex difference image and the first flow-encoded image to obtain a second flow-encoded image; and iv. generating a velocity encoded image from the first flow-encoded image and second flow-encoded image using phase difference processing.

2. The method of claim 1 wherein acquiring the undersampled PC-MRI data using the magnetic resonance imaging scanner comprises acquiring multidimensional (2D or 4D PC-MRI) data.

3. The method of claim 1 wherein the first convolutional neural network is an unrolled convolutional neural network.

4. The method of claim 1 wherein the first convolutional neural network is a DL-ESPIRiT network modified for PC-MRI data.

5. The method of claim 1 wherein the second convolutional neural network is an unrolled convolutional neural network.

6. The method of claim 1 wherein the second convolutional neural network is a DL-ESPIRiT network trained with CD PC-MRI data.

7. The method of claim 1 wherein reconstructing the complex difference image using the second convolutional neural network comprises inputting to the second convolutional neural network a difference of two portions of the undersampled PC-MRI data having different velocity encodings.

* * * * *